United States Patent
Allen et al.

(10) Patent No.: US 7,692,064 B2
(45) Date of Patent: Apr. 6, 2010

(54) NITROGEN TRANSPORT METABOLISM

(75) Inventors: Stephen M. Allen, Wilmington, DE (US); J. Antoni Rafalski, Wilmington, DE (US)

(73) Assignee: E.I. du Pont de Nemours and Company, Wilmington, DE (US)

(*) Notice: Subject to any disclaimer, the term of this patent is extended or adjusted under 35 U.S.C. 154(b) by 142 days.

(21) Appl. No.: 12/098,487

(22) Filed: Apr. 7, 2008

(65) Prior Publication Data

US 2008/0189807 A1 Aug. 7, 2008

Related U.S. Application Data

(60) Division of application No. 11/514,123, filed on Aug. 31, 2006, now Pat. No. 7,368,634, which is a division of application No. 11/012,668, filed on Dec. 15, 2004, now abandoned, which is a continuation-in-part of application No. 10/033,109, filed on Dec. 28, 2001, now Pat. No. 6,833,492, which is a division of application No. 09/384,625, filed on Aug. 27, 1999, now abandoned.

(60) Provisional application No. 60/098,248, filed on Aug. 28, 1998.

(51) Int. Cl.
| | |
|---|---|
| A01H 1/00 | (2006.01) |
| C07H 21/04 | (2006.01) |
| C12N 15/29 | (2006.01) |
| C12N 15/52 | (2006.01) |
| C07K 14/415 | (2006.01) |

(52) U.S. Cl. ................. 800/295; 435/6; 435/69.1; 435/468; 435/419; 435/252.3; 435/320.1; 435/183; 530/370; 536/23.6; 800/278

(58) Field of Classification Search .............. 435/6, 435/69.1, 468, 419, 252.3, 320.1, 183; 530/370; 536/23.6; 800/278
See application file for complete search history.

(56) References Cited

U.S. PATENT DOCUMENTS

2004/0214272 A1    10/2004   La Rossa et al.

OTHER PUBLICATIONS

Lin et al., PIR_80 Database, Accession No. T01260, Nature, vol. 402, pp. 761-768, 1999.*
National Center for Biotechnology Information General Identifier No. 1703292, Accession No. P54144, Jul. 15, 1998, O. Ninnemann et al., Identification of a high affinity NH4+ transporter from plants.
National Center for Biotechnology Information General Identifier No. 3335376, Accession No. AAC27177, Jul. 22, 1998, S. D. Rounsley et al., *Arabidopsis thaliana* chromosome II BAC F16M14 genomic sequence.
Anne-Marie Marini et al., A Family of Ammonium Transporters in *Saccharomyces cerevisiae*, Mol. and Cell. Biology, vol. 17(8):4282-4293, Aug. 1997.
La Rossa et al., Published Applications NA Main Database, Application No. US/10425115 filed Apr. 28, 2003, SEQ ID No. 144674.
Peer Bork, Powers and Pitfalls in Sequence Analysis: The 70% Hurdle, Genome Research, vol. 10:398-400, 2000.
Pierre Broun et al., Catalytic Plasticity of Fatty Acid Modification Enzymes Underlying Chemical Diversity of Plant Lipids, Science, vol. 282:131-133, Nov. 1998.
Wilson H. Burgess et al., Possible Dissocation of the Heparin-binding and Mitogenic Activities of Heparin-binding (Acidic Fibroblast) Growth Factor-1 from Its Receptor binding Activities by Site-directed Mutagenesis of a Single Lysine Residue, J. Cell Biol., vol. 111:2129-2138, 1990.
Eliane Lazar et al., Transforming Growth Factor alpha: Mutation of Aspartic Acid 47 and Leucine 48 Results in Different Biological Activities, Molec. and Cell Biol., vol. 8(3):1247-1252, Mar. 1988.
E. J. Hewitt et al., Nitrate Metabolism, Plant Biochemistry, Bonner and Varner eds., Academic Press, NY, pp. 633-681, 1976.
Olaf Ninnemann et al., Identification of a high affinity NH4+ transporter from plants, EMBO J., vol. 13(15):3464-3471, 1994.
Anne-Marie Marini et al., Cloning and expression of the MEP1 gene encoding an ammonium transporter in *Saccharomyces cerevisiae*, EMBO J., vol. 13(15):3456-3463, 1994.
National Center for Biotechnology Information General Identifier No. 568344, Accession No. D39189, Nov. 11, 1994, T. Sasaki et al., Rice cDNA from callus 1995.
National Center for Biotechnology Information General Identifier No. 2309655, Accession No. C25810, Aug. 6, 1997, K. Yamamoto et al., Rice cDNA from callus 1997.
National Center for Biotechnology Information General Identifier No. 5005512, Accession No. AU070277, Jun. 7, 1999, K. Yamamoto et al., Rice cDNA from mature leaf.
National Center for Biotechnology Information General Identifier No. 2160782, Accession No. AAB58937, Jun. 6, 1997, O. Ninnemann et al., Identification of a high affinity NH4+ transporter from plants.

* cited by examiner

*Primary Examiner*—Phuong T Bui

(57) ABSTRACT

This invention relates to an isolated nucleic acid fragments encoding an ammonium transporter. The invention also relates to the construction of a recombinant DNA constructencoding all or a portion of ammonium transporters, in sense or antisense orientation, wherein expression of the recombinant DNA construct may alter levels of the ammonium transporter in a transformed host cell.

11 Claims, No Drawings

SEQUENCE LISTING

<160> NUMBER OF SEQ ID NOS: 16

<210> SEQ ID NO 1
<211> LENGTH: 1037
<212> TYPE: DNA
<213> ORGANISM: Zea mays

<400> SEQUENCE: 1

```
gcacgaggtt cgcggccatc acggccgggt gcagcgtggt ggagccgtgg gcggccgtca        60
tctgcgggtt cgtgtccgcg tgggtgctca tcggcgccaa cgccctcgcg gcgcgcttca       120
ggttcgacga cccgctggag gcggcgcagc tgcacggcgg gtgtggcgcc tggggcgtcc       180
tcttcacggg gctcttcgcg aggcgaaagt acgtggagga gatctacggc gccgggaggc       240
cctacgggct gttcatgggc ggcggcggga agctcctcgc cgcgcagatc atccagatcc       300
tggtgatcgc cgggtgggtg agctgcacca tgggcccgct cttctacgcg ctcaagaagc       360
tgggcctgct gcgcatctcg gccgacgacg agatgtccgg catggacctg acccggcacg       420
gcggcttcgc ctacgtctac cacgacgagg accctggcga caaggccggg gttggtgggt       480
tcatgctcaa gtccgcgcag aaccgtgtcg agccggcggc ggcggtggcg gcggcgacca       540
gcagccaggt gtaaaaaaaa aatcaggagc aaattgaaac cgagctgaag ttacgtgctt       600
gcctttttca gtatgttgtc gcgtatcacg tttgaggtgg atcgtatctg ccggtcagta       660
cgcagtgttt gggcaaatac ttggctactt gggagtcgca agaaattgtg taaattatat       720
agaggaggat ggcgacgaag cacgcatgtg ttacgtagtt ggggtttgtg tgcacatggt       780
ggtgggcagg ggctaggaga gggtttatct ttaggttatt ttcgtagtgg aatgaatctt       840
atgatcggat atccatcgtc ggaaggtgtg gcgggctgct ggtcaagata ggtggcttct       900
atgactatga gggttgaaac aacaagtgga cgattctgtc ctgtggtcac tgctcatcat       960
ccaatctagc ggctttgacg gtcgtgcctt tttagtatca ataatattat tccaagttta      1020
aaaaaaaaaa aaaaaaa                                                     1037
```

<210> SEQ ID NO 2
<211> LENGTH: 183
<212> TYPE: PRT
<213> ORGANISM: Zea mays

-continued

<400> SEQUENCE: 2

Thr Arg Phe Ala Ala Ile Thr Ala Gly Cys Ser Val Val Glu Pro Trp
1               5                   10                  15

Ala Ala Val Ile Cys Gly Phe Val Ser Ala Trp Val Leu Ile Gly Ala
            20                  25                  30

Asn Ala Leu Ala Ala Arg Phe Arg Phe Asp Asp Pro Leu Glu Ala Ala
        35                  40                  45

Gln Leu His Gly Gly Cys Gly Ala Trp Gly Val Leu Phe Thr Gly Leu
    50                  55                  60

Phe Ala Arg Arg Lys Tyr Val Glu Glu Ile Tyr Gly Ala Gly Arg Pro
65                  70                  75                  80

Tyr Gly Leu Phe Met Gly Gly Gly Gly Lys Leu Leu Ala Ala Gln Ile
                85                  90                  95

Ile Gln Ile Leu Val Ile Ala Gly Trp Val Ser Cys Thr Met Gly Pro
            100                 105                 110

Leu Phe Tyr Ala Leu Lys Lys Leu Gly Leu Leu Arg Ile Ser Ala Asp
        115                 120                 125

Asp Glu Met Ser Gly Met Asp Leu Thr Arg His Gly Gly Phe Ala Tyr
    130                 135                 140

Val Tyr His Asp Glu Asp Pro Gly Asp Lys Ala Gly Val Gly Gly Phe
145                 150                 155                 160

Met Leu Lys Ser Ala Gln Asn Arg Val Glu Pro Ala Ala Ala Val Ala
                165                 170                 175

Ala Ala Thr Ser Ser Gln Val
            180

<210> SEQ ID NO 3
<211> LENGTH: 1706
<212> TYPE: DNA
<213> ORGANISM: Glycine max

<400> SEQUENCE: 3
gcacgagcac tcccaaccc cacccgtagt ttctaccacc ttcagtcacg gcgtaataca      60
ctaaccaacc caccatgtcg ctgcctgctt gtcccgccga caactggcc caacttctcg     120 gcccaaacac cacagacgcc tccgccgccg cctcccttat ctgcggccat ttcgccgccg    180
tggacagcaa gttcgtcgac acggccttcg ccgtcgacaa cacctacctc ctcttttccg    240
cctacctcgt ttttctatg cagctcggct tcgccatgct ctgcgccggc tccgtccgcg     300
ccaagaacac catgaacatc atgctcacca acgtcctgga cgctgccgcc ggcggcctct    360
tctactacct cttcggcttc gccttcgctt tcggctcccc ctccaacggc ttcatcggta    420
aacatttctt cggcctcaag gacatccctt catcctcca cgactacagc tacttcctct    480
accaatgggc cttcgccatc gccgccgccg gcatcaccag cggaagcatc gccgaacgca    540
cacagttcgt ggcctatctc atctactcct ccttcctcac cggcttcgtc tatccggtgg    600
tctcccactg gttctggtcc ccagacggct gggcctctgc ctttaagatc accgaccggc    660
tattttccac cggcgtaata gacttcgccg gttccggcgt agtccacatg gtcggcggaa    720
tagccggcct atggggagcg ctgatcgaag gcccaagaat gggacgtttc gatcatgcag    780
gacgagctgt ggccttgcga ggccacagcg cgtccttagt agtcctggga accttcttgc    840
tttggttcgg ttggtacgga tttaaccccg gttcatttaa caaaatccta cttacttacg    900
gtaactcagg aaaattactac ggtcaatgga gcgcggttgg cagaaccgcg gtcaccacta    960 cccttagcggg gtcaacagct gccttgacca cgctattcgg taaacgggtg atatccggtc   1020

```
actggaacgt gaccgatgtc tgcaacgggc tgttaggcgg tttcgcggcg ataacagccg   1080
gttgctccgt ggttgagcca tgggcagcca tcgtatgcgg ttttgttgct tctatagtat   1140
taatagcttg caacaaatta gcagagaagg ttaagttcga cgatcctctg gaggcggcgc   1200
agttgcacgg tgggtgtggc acgtgggggg tgatattcac ggcgttgttc gcaaaaaagg   1260
agtatgtgaa ggaggtttac gggttgggga gggcgcacgg gttgctcatg ggggtggtg   1320 ggaagttgct ggcggcgcac gtgattcaga ttctggtgat tgctgggtgg gttagtgcga   1380
ccatgggacc cttgttttgg gggttgaata aactgaagct gttgaggatt cttcagagg   1440 atgagcttgc ggggatggac atgactcgcc atggaggctt tgcttatgct tatgaggatg   1500
atgagacgca caagcatggg atgcagttga ggagggttgg gcccaacgcg tcttccacac   1560
ccaccactga tgaatgatct ttttttccca tatgcatgtc tcattagtca acattaaat    1620 ttggatacat attccttgta aggattcaaa ccttggttac ttgttacttc tgttaaaaaa   1680
aaaaaaaaaa aaaaaaaaa aaaaa                                          1706
```

<210> SEQ ID NO 4
<211> LENGTH: 500
<212> TYPE: PRT
<213> ORGANISM: Glycine max

<400> SEQUENCE: 4

```
Met Ser Leu Pro Ala Cys Pro Ala Glu Gln Leu Ala Gln Leu Leu Gly
  1               5                  10                  15

Pro Asn Thr Thr Asp Ala Ser Ala Ala Ser Leu Ile Cys Gly His
             20                  25                  30

Phe Ala Ala Val Asp Ser Lys Phe Val Asp Thr Ala Phe Ala Val Asp
         35                  40                  45

Asn Thr Tyr Leu Leu Phe Ser Ala Tyr Leu Val Phe Ser Met Gln Leu
     50                  55                  60

Gly Phe Ala Met Leu Cys Ala Gly Ser Val Arg Ala Lys Asn Thr Met
 65                  70                  75                  80

Asn Ile Met Leu Thr Asn Val Leu Asp Ala Ala Gly Gly Leu Phe
                 85                  90                  95

Tyr Tyr Leu Phe Gly Phe Ala Phe Ala Phe Gly Ser Pro Ser Asn Gly
                100                 105                 110

Phe Ile Gly Lys His Phe Phe Gly Leu Lys Asp Ile Pro Ser Ser Ser
            115                 120                 125

Tyr Asp Tyr Ser Tyr Phe Leu Tyr Gln Trp Ala Phe Ala Ile Ala Ala
        130                 135                 140

Ala Gly Ile Thr Ser Gly Ser Ile Ala Glu Arg Thr Gln Phe Val Ala
145                 150                 155                 160

Tyr Leu Ile Tyr Ser Ser Phe Leu Thr Gly Phe Val Tyr Pro Val Val
                165                 170                 175

Ser His Trp Phe Trp Ser Pro Asp Gly Trp Ala Ser Ala Phe Lys Ile
            180                 185                 190

Thr Asp Arg Leu Phe Ser Thr Gly Val Ile Asp Phe Ala Gly Ser Gly
        195                 200                 205

Val Val His Met Val Gly Gly Ile Ala Gly Leu Trp Gly Ala Leu Ile
    210                 215                 220

Glu Gly Pro Arg Met Gly Arg Phe Asp His Ala Gly Arg Ala Val Ala
225                 230                 235                 240

Leu Arg Gly His Ser Ala Ser Leu Val Val Leu Gly Thr Phe Leu Leu
```

-continued

```
                245                 250                 255
Trp Phe Gly Trp Tyr Gly Phe Asn Pro Gly Ser Phe Asn Lys Ile Leu
            260                 265                 270
Leu Thr Tyr Gly Asn Ser Gly Asn Tyr Tyr Gly Gln Trp Ser Ala Val
        275                 280                 285
Gly Arg Thr Ala Val Thr Thr Leu Ala Gly Ser Thr Ala Ala Leu
    290                 295                 300
Thr Thr Leu Phe Gly Lys Arg Val Ile Ser Gly His Trp Asn Val Thr
305                 310                 315                 320
Asp Val Cys Asn Gly Leu Leu Gly Gly Phe Ala Ala Ile Thr Ala Gly
                325                 330                 335
Cys Ser Val Val Glu Pro Trp Ala Ala Ile Val Cys Gly Phe Val Ala
            340                 345                 350
Ser Ile Val Leu Ile Ala Cys Asn Lys Leu Ala Glu Lys Val Lys Phe
        355                 360                 365
Asp Asp Pro Leu Glu Ala Ala Gln Leu His Gly Gly Cys Gly Thr Trp
    370                 375                 380
Gly Val Ile Phe Thr Ala Leu Phe Ala Lys Lys Glu Tyr Val Lys Glu
385                 390                 395                 400
Val Tyr Gly Leu Gly Arg Ala His Gly Leu Leu Met Gly Gly Gly Gly
                405                 410                 415
Lys Leu Leu Ala Ala His Val Ile Gln Ile Leu Val Ile Ala Gly Trp
            420                 425                 430
Val Ser Ala Thr Met Gly Pro Leu Phe Trp Gly Leu Asn Lys Leu Lys
        435                 440                 445
Leu Leu Arg Ile Ser Ser Glu Asp Glu Leu Ala Gly Met Asp Met Thr
    450                 455                 460
Arg His Gly Gly Phe Ala Tyr Ala Tyr Glu Asp Asp Glu Thr His Lys
465                 470                 475                 480
His Gly Met Gln Leu Arg Arg Val Gly Pro Asn Ala Ser Ser Thr Pro
                485                 490                 495
Thr Thr Asp Glu
            500
```

<210> SEQ ID NO 5
<211> LENGTH: 1991
<212> TYPE: DNA
<213> ORGANISM: Triticum aestivum

<400> SEQUENCE: 5

| | | | | | |
|---|---|---|---|---|---|
| gccaatcccg | gcttcccgat | tccgatcgct | gaacgccaac | cactttccta | agcagggggg | 60 |
| cgccgcggag | atgtcggcga | cgtgcgcggc | ggacctgggg | ccgctgctgg | gggcggcggc | 120 |
| ggcgaacgcc | acggactacc | tgtgcaacag | gttcgccgac | accacgtccg | cggtggactc | 180 |
| cacctacctg | ctcttctcgg | cctacctcgt | cttcgccatg | cagctcggct | cgccatgct | 240 |
| ctgcgccggc | tccgtccggg | ccaagaacac | catgaacatc | atgctcacca | acgtgctcga | 300 |
| cgccgccgcc | ggcgcgctct | tctactacct | cttcggcttc | gccttcgcct | cgggacgcc | 360 |
| gtcgaacggc | ttcatcggga | agcacttctt | cggcctcaag | gacatgccgc | agaccggctt | 420 |
| cgactacagc | ttcttcctct | tccagtgggg | cttcgccatc | gccgccgccg | gcatcacctc | 480 |
| cggctccatc | gccgagagga | cgcagttcgt | cgcgtatctc | atctactcgg | ccttccttac | 540 |
| gggattcgtc | tacccggtcg | tgtcccactg | gatctggtcc | gtcgacggct | gggctccgc | 600 |
| ggcccgcacg | tccggcccgc | tgctcttcaa | gtccggcgtg | atcgacttcg | ccggctccgg | 660 |

```
cgtcgtgcac atggtcggcg gcatcgccgg cttctggggc gcgctcatcg agggccccg    720
catcggccgg ttcgaccacg ccggccgctc ggtggcgctc aagggccaca gcgcgtcgct    780
cgtcgtgctg gggaccttcc tgctctggtt cggctggtac gggttcaacc cggggtcctt    840
cgtcaccatc ctcaagtcgt acggcccgcc cgggagcatc aacgggcagt ggtcgggcgt    900
gggccgcacc gccgtgacga cgacgctggc gggcagcgtg gcggcgctca cgacgctgtt    960
cgggaagcgg ctccagacgg ggcactggaa cgtggtggac gtctgcaacg gcctgctcgg   1020
cgggttcgcg gccatcaccg ccgggtgcag cgtggtcgac ccgtgggccg ccgtcatctg   1080
cggcttcgtc tccgcctggg tgctcatcgg gctcaacgcg ctcgccggcc gcctcaagta   1140
cgacgacccg ctggaggcgg cgcagctgca cggcggctgc ggcgcgtggg ggatcatctt   1200
cacggcgctg ttcgccaaga agcagtacgt ggaggagatc tacggcgccg gcaggccgta   1260
cgggctgttc ctgggcggcg gcgggcggct gctggcggcg cacatcgtgc agatcctcgt   1320
catcgccggc ttcgtgagct gcaccatggg cccgctcttc ttggcgctca agaagctggg   1380
cctgctccgc atctcggccg aggacgagat ggccggcatg gacctgaccc ggcacggtgg   1440
gttcgcctac gtctaccacg acgacgacga gcacgacaag tcggtcggcg gcttcatgct   1500
caggtcggcg cagacccgcg tcgagccggc ggcggcggcg aacagccagg tctaaccaat   1560
caagccggac tacgtaacaa gaaatccagt ggaaatcgcc tttctgttct cgcgcgtcat   1620
atcacatatg tgatccgatc atgggatcaa tatttccggt gctgtttggg ccaatacttt   1680
ggcgctcttg tgttcgttca caagattgta aaattattac actaggacga ggttattttt   1740
tttacctttt ttgtgtacat gcgtgcgttt agaggagatg tgtggtgtgt ggatggaatc   1800
tgcagggctg gggttttttc tttcttggtg atatcttgtc atttttgtgg tggaattttg   1860
tgatcatgag ggtgtggtca agataggtgg ctgctcaagg ttgaattgtt gagatttgtc   1920
ctctagtacg ggccaccctc tctatcaaaa ctttggcgcg ttttctcgat cgaaaaaaaa   1980
aaaaaaaaaa a                                                        1991

<210> SEQ ID NO 6
<211> LENGTH: 494
<212> TYPE: PRT
<213> ORGANISM: Triticum aestivum

<400> SEQUENCE: 6

Met Ser Ala Thr Cys Ala Ala Asp Leu Gly Pro Leu Gly Ala Ala
  1               5                  10                  15

Ala Ala Asn Ala Thr Asp Tyr Leu Cys Asn Arg Phe Ala Asp Thr Thr
                 20                  25                  30

Ser Ala Val Asp Ser Thr Tyr Leu Leu Phe Ser Ala Tyr Leu Val Phe
             35                  40                  45

Ala Met Gln Leu Gly Phe Ala Met Leu Cys Ala Gly Ser Val Arg Ala
         50                  55                  60

Lys Asn Thr Met Asn Ile Met Leu Thr Asn Val Leu Asp Ala Ala Ala
 65                  70                  75                  80

Gly Ala Leu Phe Tyr Tyr Leu Phe Gly Phe Ala Phe Ala Phe Gly Thr
                 85                  90                  95

Pro Ser Asn Gly Phe Ile Gly Lys His Phe Phe Gly Leu Lys Asp Met
                100                 105                 110

Pro Gln Thr Gly Phe Asp Tyr Ser Phe Phe Leu Phe Gln Trp Ala Phe
            115                 120                 125
```

-continued

```
Ala Ile Ala Ala Gly Ile Thr Ser Gly Ser Ile Ala Glu Arg Thr
    130                 135                 140
Gln Phe Val Ala Tyr Leu Ile Tyr Ser Ala Phe Leu Thr Gly Phe Val
145                 150                 155                 160
Tyr Pro Val Val Ser His Trp Ile Trp Ser Val Asp Gly Trp Ala Ser
                165                 170                 175
Ala Ala Arg Thr Ser Gly Pro Leu Leu Phe Lys Ser Gly Val Ile Asp
            180                 185                 190
Phe Ala Gly Ser Gly Val Val His Met Val Gly Gly Ile Ala Gly Phe
        195                 200                 205
Trp Gly Ala Leu Ile Glu Gly Pro Arg Ile Gly Arg Phe Asp His Ala
210                 215                 220
Gly Arg Ser Val Ala Leu Lys Gly His Ser Ala Ser Leu Val Val Leu
225                 230                 235                 240
Gly Thr Phe Leu Leu Trp Phe Gly Trp Tyr Gly Phe Asn Pro Gly Ser
                245                 250                 255
Phe Val Thr Ile Leu Lys Ser Tyr Gly Pro Pro Gly Ser Ile Asn Gly
            260                 265                 270
Gln Trp Ser Gly Val Gly Arg Thr Ala Val Thr Thr Thr Leu Ala Gly
        275                 280                 285
Ser Val Ala Ala Leu Thr Thr Leu Phe Gly Lys Arg Leu Gln Thr Gly
290                 295                 300
His Trp Asn Val Val Asp Val Cys Asn Gly Leu Leu Gly Gly Phe Ala
305                 310                 315                 320
Ala Ile Thr Ala Gly Cys Ser Val Val Asp Pro Trp Ala Ala Val Ile
                325                 330                 335
Cys Gly Phe Val Ser Ala Trp Val Leu Ile Gly Leu Asn Ala Leu Ala
            340                 345                 350
Gly Arg Leu Lys Tyr Asp Asp Pro Leu Glu Ala Ala Gln Leu His Gly
        355                 360                 365
Gly Cys Gly Ala Trp Gly Ile Ile Phe Thr Ala Leu Phe Ala Lys Lys
    370                 375                 380
Gln Tyr Val Glu Glu Ile Tyr Gly Ala Gly Arg Pro Tyr Gly Leu Phe
385                 390                 395                 400
Leu Gly Gly Gly Arg Leu Leu Ala Ala His Ile Val Gln Ile Leu
                405                 410                 415
Val Ile Ala Gly Phe Val Ser Cys Thr Met Gly Pro Leu Phe Leu Ala
            420                 425                 430
Leu Lys Lys Leu Gly Leu Leu Arg Ile Ser Ala Glu Asp Glu Met Ala
        435                 440                 445
Gly Met Asp Leu Thr Arg His Gly Gly Phe Ala Tyr Val Tyr His Asp
    450                 455                 460
Asp Asp Glu His Asp Lys Ser Val Gly Gly Phe Met Leu Arg Ser Ala
465                 470                 475                 480
Gln Thr Arg Val Glu Pro Ala Ala Ala Ala Asn Ser Gln Val
                485                 490
```

<210> SEQ ID NO 7
<211> LENGTH: 376
<212> TYPE: DNA
<213> ORGANISM: Zea mays
<220> FEATURE:
<221> NAME/KEY: misc_feature
<222> LOCATION: (40)..(40)
<223> OTHER INFORMATION: n is a, c, g, or t
<220> FEATURE:

```
<221> NAME/KEY: misc_feature
<222> LOCATION: (272)..(272)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (359)..(359)
<223> OTHER INFORMATION: n is a, c, g, or t
<220> FEATURE:
<221> NAME/KEY: misc_feature
<222> LOCATION: (361)..(361)
<223> OTHER INFORMATION: n is a, c, g, or t

<400> SEQUENCE: 7
gctaagagag agagagagag agaggtatac gtaggaccgn cggcaactag ctaactaaca      60
tgtcgtcgtc gtccgggacg acgatgccgc tggcgtacca gacgtcggcg tcgtctcccg     120
agtggctgaa caagggcgac aacgcgtggc agctgacggc ggcgacgctg gtggggctgc     180
agagcttccc gggtctggtg gtcctgtacg gcggcgtggt gaagaagaag tgggccgtga     240
actcggcctt catggcgctg tacgcgttcg cnggcnggtg tggatctgct gggngacctg     300
ggcctacaac atgtcctttg gcgaacaggg ctgctgtcng ntgtggggca aaggcggcng     360
ncggtgctta atccag                                                    376

<210> SEQ ID NO 8
<211> LENGTH: 63
<212> TYPE: PRT
<213> ORGANISM: Zea mays

<400> SEQUENCE: 8

Met Pro Leu Ala Tyr Gln Thr Ser Ala Ser Ser Pro Glu Trp Leu Asn
  1               5                  10                  15

Lys Gly Asp Asn Ala Trp Gln Leu Thr Ala Ala Thr Leu Val Gly Leu
             20                  25                  30

Gln Ser Phe Pro Gly Leu Val Val Leu Tyr Gly Gly Val Val Lys Lys
         35                  40                  45

Lys Trp Ala Val Asn Ser Ala Phe Met Ala Leu Tyr Ala Phe Ala
     50                  55                  60

<210> SEQ ID NO 9
<211> LENGTH: 1883
<212> TYPE: DNA
<213> ORGANISM: Oryza sativa

<400> SEQUENCE: 9
gcacgagctt acatgtaagc tcgtgccgaa ttcggcacga gcttacaatc caaacaatca      60
cgtcggtcga cgagaagaag tgagtgatgg cgtcgccgac ccggccgggg ccgtacatgc     120
cgcgcccacc ggcggtgccg gagtggctga acaccgggga caacgggtgg cagctcgcgg     180
cggcgacgtt cgtcgggctc cagtcgatgc ctgggctggt ggtgctgtac ggcagcatcg     240
```

-continued

```
tgaagaagaa gtgggccgtc aactcggcct tcatggcgct gtacgcgtac gcgtccacgc      300
tcatcgtgtg ggtgctggtc ggcttccgca tggcgttcgg cgaccggctg ctcccgttct      360
gggggaaggc cggcgcggcg ctgacggagg ggttcctcgt ggcgcgcgcg tcggtcccgg      420
ccacggcgca ctacgggaag gacggcgccc tggagtcgcc gcgcaccgag ccgttctacc      480
cggaggcgtc catggtgctg ttccagttcg agctcgccgc catcacgctg gtgctgctcg      540
ccgggtcgct cctcgggagg atgaacatca aggcgtggat ggcgttcact ccgctctggc      600
tcctcttctc ctacaccgtc tgcgccttca gcctctgggg cggcggcttc ctctaccagt      660
ggggcgtcat cgactactcc ggcggatacg tcatccacct ctcctccggc atcgccggct      720
tcaccgccgc ctactgggtg gggccgaggc tgaagagcga cagggagcgg ttctcgccga      780
acaacatcct cctcatgatc gccggcggcg gctgctgtg gctgggctgg gccgggttca      840
acggcggcgc gccgtacgcc ccaaacatca ccgcgtccat cgccgtgctc aacaccaacg      900
tcagcgccgc ggcgagcctc ctcacctgga cctgcctcga cgtcatcttc ttcggcaagc      960
cctccgtcat cggcgccgtg cagggcatga tgaccggtct cgtctgcatc accccggcg     1020 caggtctggt gcacacgtgg gcggccatac tgatgggcat ctgtggcggc agcttgccgt     1080
ggttctccat gatgatcctc acaagagat cggcgctgct ccagaaggtg gacgacaccc     1140
tcgccgtctt ccacacccac gccgtcgcgg gcctcctcgg cggcttcctc acgggcctgt     1200
tcgccttgcc ggacctcacc gccgtccaca cccacatccc tggcgcgcgc ggcgcgttct     1260
acggcggcgg catcgcccag gtggggaagc agatcgccgc cgcgctcttc gtcgtcgtgt     1320
ggaacgtcgt ggccaccacc gtcatcctgc tcggcgtcgg cctcgtcgtc ccgctccgca     1380
tgcccgacga gcagctcaag atcggcgacg acgcggcgca cggggaggag gcctacgcgc     1440
tatggggaga cggcgagagg ttcgacgtga cgcgccatga gggggcgagg ggcggcgcgt     1500
ggggcgccgc ggtcgtggac gaggcgatgg atcaccggct ggccggaatg ggagcgagag     1560
gagtcacgat tcagctgtag tggtggtaga gtgggcattt tgtcgcaggc tttgccgcac     1620
tgcagctaaa ctggacgttg accatacgat aattctcatc tcgtacaggt agatcttgca     1680
actagcaaga tggagtagca gatattacta aacacatatg cttcattatt ttatttctgg     1740
agtaaatcaa gattcgtttt ggggtagtgg tagatatttg caatctgatg cagtcagtat     1800
gcaatgtgtc ctaccctggg agtcccaata gataaacaaa cttttgccag cattgcacac     1860
aagcaaaaaa aaaaaaaaaa aaa                                             1883
```

<210> SEQ ID NO 10
<211> LENGTH: 497
<212> TYPE: PRT
<213> ORGANISM: Oryza sativa

<400> SEQUENCE: 10

```
Met Ala Ser Pro Thr Arg Pro Gly Pro Tyr Met Pro Arg Pro Pro Ala
  1               5                  10                  15

Val Pro Glu Trp Leu Asn Thr Gly Asp Asn Gly Trp Gln Leu Ala Ala
             20                  25                  30

Ala Thr Phe Val Gly Leu Gln Ser Met Pro Gly Leu Val Val Leu Tyr
         35                  40                  45

Gly Ser Ile Val Lys Lys Lys Trp Ala Val Asn Ser Ala Phe Met Ala
     50                  55                  60

Leu Tyr Ala Tyr Ala Ser Thr Leu Ile Val Trp Val Leu Val Gly Phe
 65                  70                  75                  80
```

```
Arg Met Ala Phe Gly Asp Arg Leu Leu Pro Phe Trp Gly Lys Ala Gly
                85                  90                  95

Ala Ala Leu Thr Glu Gly Phe Leu Val Ala Arg Ala Ser Val Pro Ala
            100                 105                 110

Thr Ala His Tyr Gly Lys Asp Gly Ala Leu Glu Ser Pro Arg Thr Glu
        115                 120                 125

Pro Phe Tyr Pro Glu Ala Ser Met Val Leu Phe Gln Phe Glu Leu Ala
    130                 135                 140

Ala Ile Thr Leu Val Leu Leu Ala Gly Ser Leu Leu Gly Arg Met Asn
145                 150                 155                 160

Ile Lys Ala Trp Met Ala Phe Thr Pro Leu Trp Leu Leu Phe Ser Tyr
                165                 170                 175

Thr Val Cys Ala Phe Ser Leu Trp Gly Gly Phe Leu Tyr Gln Trp
            180                 185                 190

Gly Val Ile Asp Tyr Ser Gly Gly Tyr Val Ile His Leu Ser Ser Gly
        195                 200                 205

Ile Ala Gly Phe Thr Ala Ala Tyr Trp Val Gly Pro Arg Leu Lys Ser
    210                 215                 220

Asp Arg Glu Arg Phe Ser Pro Asn Asn Ile Leu Leu Met Ile Ala Gly
225                 230                 235                 240

Gly Gly Leu Leu Trp Leu Gly Trp Ala Gly Phe Asn Gly Gly Ala Pro
                245                 250                 255

Tyr Ala Pro Asn Ile Thr Ala Ser Ile Ala Val Leu Asn Thr Asn Val
            260                 265                 270

Ser Ala Ala Ala Ser Leu Leu Thr Trp Thr Cys Leu Asp Val Ile Phe
        275                 280                 285

Phe Gly Lys Pro Ser Val Ile Gly Ala Val Gln Gly Met Met Thr Gly
    290                 295                 300

Leu Val Cys Ile Thr Pro Gly Ala Gly Leu Val His Thr Trp Ala Ala
305                 310                 315                 320

Ile Leu Met Gly Ile Cys Gly Gly Ser Leu Pro Trp Phe Ser Met Met
                325                 330                 335

Ile Leu His Lys Arg Ser Ala Leu Leu Gln Lys Val Asp Asp Thr Leu
            340                 345                 350

Ala Val Phe His Thr His Ala Val Ala Gly Leu Leu Gly Gly Phe Leu
        355                 360                 365

Thr Gly Leu Phe Ala Leu Pro Asp Leu Thr Ala Val His Thr His Ile
    370                 375                 380

Pro Gly Ala Arg Gly Ala Phe Tyr Gly Gly Gly Ile Ala Gln Val Gly
385                 390                 395                 400

Lys Gln Ile Ala Gly Ala Leu Phe Val Val Trp Asn Val Val Ala
                405                 410                 415

Thr Thr Val Ile Leu Leu Gly Val Gly Leu Val Val Pro Leu Arg Met
            420                 425                 430

Pro Asp Glu Gln Leu Lys Ile Gly Asp Asp Ala Ala His Gly Glu Glu
        435                 440                 445

Ala Tyr Ala Leu Trp Gly Asp Gly Glu Arg Phe Asp Val Thr Arg His
    450                 455                 460

Glu Gly Ala Arg Gly Gly Ala Trp Gly Ala Val Val Asp Glu Ala
465                 470                 475                 480

Met Asp His Arg Leu Ala Gly Met Gly Ala Arg Gly Val Thr Ile Gln
                485                 490                 495
```

Leu

<210> SEQ ID NO 11
<211> LENGTH: 1961
<212> TYPE: DNA
<213> ORGANISM: Glycine max

<400> SEQUENCE: 11

| | | | | | |
|---|---|---|---|---|---|
| gcacgagtca | cgatcagaca | ttaaatgtaa | acacttctct | atcaaaaatt | tgaacttagt | 60 |
| tcgcctcaca | cttttgtttt | gtcaccttgt | gagagactaa | ttccctctaa | taaacgcaac | 120 |
| gttgttcatc | agtggcacat | acatatacag | catcacaatt | ctttgaaggg | tgaaaaagct | 180 |
| tgatcaagaa | ttgaagcata | ttgatcttca | gccatggcta | cacccttggc | ctaccaagag | 240 |
| caccttccgg | cggcacccga | atggctgaac | aaaggtgaca | acgcatggca | gctaacagca | 300 |
| gccaccctcg | tcggtcttca | aagcatgccg | ggtctcgtga | tcctctacgc | cagcatagtg | 360 |
| aagaaaaaat | gggcagtgaa | ctcagctttc | atggctctct | acgcctttgc | ggcggttcta | 420 |
| atatgttggg | tgcttgtgtg | ttaccgaatg | gcctttggag | aagaactttt | cccccttctgg | 480 |
| ggaaagggtg | ctccagcact | aggccagaag | ttcctcacga | aaagagccat | agtcattgaa | 540 |
| accatccacc | actttgataa | tggcactgtt | gaatcacctc | ctgaggaacc | cttttaccct | 600 |
| atggcctcgc | ttgtgtattt | ccaattcact | tttgctgcta | ttactcttat | tttgttggct | 660 |
| ggctctgtcc | ttggccgaat | gaacatcaag | gcttggatgg | cttttgtgcc | tctttggttg | 720 |
| atcttttcct | acacagtcgg | ggcttttagt | cttggggtg | gtggctttct | ctaccaatgg | 780 |
| ggcgttattg | attattctgg | cggctatgtc | atacaccttt | cttctggaat | cgctggcttc | 840 |
| actgctgctt | actgggttgg | accaaggttg | aagagtgata | gggagaggtt | cccaccaaac | 900 |
| aatgtgcttc | tcatgcttgc | tggtgctggg | ttgttgtgga | tggggtggtc | agggttcaac | 960 |
| ggtggagcac | catatgctgc | aaacattgca | tcttcaattg | cggtgttgaa | cacaaacatt | 1020 |
| tgtgcagcca | ctagcctcct | tgtgtggaca | actttggatg | tcattttttt | tgggaaacct | 1080 |
| tcggtgattg | gagctgtgca | gggcatgatg | actgacttg | tatgcatcac | ccagggggca | 1140 |
| gggcttgtgc | aatcatgggc | tgctatagtg | atgggaatat | tatctgggag | cattccatgg | 1200 |
| gtgactatga | tgattttgca | taaaaagtca | actttgctac | agaaggtaga | tgacacccttt | 1260 |
| ggtgtgtttc | acacacatgc | tgtggctggc | cttttgggtg | gtctcctcac | aggtctatta | 1320 |
| gcagaaccag | ccctttgtag | acttctattg | ccagtaacaa | attcaagggg | tgcattctat | 1380 |
| ggtggaggtg | gtggtgtgca | gttcttcaag | caattggtgg | cggccatgtt | tgttattgga | 1440 |
| tggaacttgg | tgtccaccac | cattattctc | cttgtcataa | aattgttcat | acccttgagg | 1500 |
| atgccggacg | agcagctgga | aatcggtgac | gacgccgtcc | acggtgagga | agcttatgcc | 1560 |
| ctttgggggtg | atggagaaaa | atatgaccca | actaggcatg | gttccttgca | aagtggcaac | 1620 |
| actactgtct | caccttatgt | taatggtgca | agaggggtga | ctataaaactt | atgagtcaag | 1680 |
| aaattaggct | gtgccttgct | cacacatgca | tgtgtataaa | tttatatgat | taacaaatgt | 1740 |
| gatgaatccg | tgagtggtat | aagtagatat | ttgattttgt | catgaaagaa | aatttccaaa | 1800 |
| ttttgagatc | tgatgttcct | ctggtcatct | tgcattcgaa | gacctggtca | tatatttctg | 1860 |
| gcacagaatg | tcttggcatg | tgtataaaat | ttagatttgt | caaattttaa | aggaacttat | 1920 |
| gattagtttt | tttcacttag | aagaaaaaaa | aaaaaaaaaa | a | | 1961 |

<210> SEQ ID NO 12
<211> LENGTH: 486

```
<212> TYPE: PRT
<213> ORGANISM: Glycine max

<400> SEQUENCE: 12

Met Ala Thr Pro Leu Ala Tyr Gln Glu His Leu Pro Ala Ala Pro Glu
  1               5                  10                  15

Trp Leu Asn Lys Gly Asp Asn Ala Trp Gln Leu Thr Ala Ala Thr Leu
             20                  25                  30

Val Gly Leu Gln Ser Met Pro Gly Leu Val Ile Leu Tyr Ala Ser Ile
         35                  40                  45

Val Lys Lys Lys Trp Ala Val Asn Ser Ala Phe Met Ala Leu Tyr Ala
     50                  55                  60

Phe Ala Ala Val Leu Ile Cys Trp Val Leu Val Cys Tyr Arg Met Ala
 65                  70                  75                  80

Phe Gly Glu Glu Leu Phe Pro Phe Trp Gly Lys Gly Ala Pro Ala Leu
                 85                  90                  95

Gly Gln Lys Phe Leu Thr Lys Arg Ala Ile Val Ile Glu Thr Ile His
            100                 105                 110

His Phe Asp Asn Gly Thr Val Glu Ser Pro Glu Glu Pro Phe Tyr
        115                 120                 125

Pro Met Ala Ser Leu Val Tyr Phe Gln Phe Thr Phe Ala Ala Ile Thr
    130                 135                 140

Leu Ile Leu Leu Ala Gly Ser Val Leu Gly Arg Met Asn Ile Lys Ala
145                 150                 155                 160

Trp Met Ala Phe Val Pro Leu Trp Leu Ile Phe Ser Tyr Thr Val Gly
                165                 170                 175

Ala Phe Ser Leu Trp Gly Gly Phe Leu Tyr Gln Trp Gly Val Ile
                180                 185                 190

Asp Tyr Ser Gly Gly Tyr Val Ile His Leu Ser Ser Gly Ile Ala Gly
            195                 200                 205

Phe Thr Ala Ala Tyr Trp Val Gly Pro Arg Leu Lys Ser Asp Arg Glu
210                 215                 220

Arg Phe Pro Pro Asn Asn Val Leu Leu Met Leu Ala Gly Ala Gly Leu
225                 230                 235                 240

Leu Trp Met Gly Trp Ser Gly Phe Asn Gly Gly Ala Pro Tyr Ala Ala
                245                 250                 255

Asn Ile Ala Ser Ser Ile Ala Val Leu Asn Thr Asn Ile Cys Ala Ala
            260                 265                 270

Thr Ser Leu Leu Val Trp Thr Thr Leu Asp Val Ile Phe Phe Gly Lys
        275                 280                 285

Pro Ser Val Ile Gly Ala Val Gln Gly Met Met Thr Gly Leu Val Cys
    290                 295                 300

Ile Thr Pro Gly Ala Gly Leu Val Gln Ser Trp Ala Ala Ile Val Met
305                 310                 315                 320

Gly Ile Leu Ser Gly Ser Ile Pro Trp Val Thr Met Met Ile Leu His
                325                 330                 335

Lys Lys Ser Thr Leu Leu Gln Lys Val Asp Asp Thr Leu Gly Val Phe
            340                 345                 350

His Thr His Ala Val Ala Gly Leu Leu Gly Gly Leu Leu Thr Gly Leu
        355                 360                 365

Leu Ala Glu Pro Ala Leu Cys Arg Leu Leu Pro Val Thr Asn Ser
    370                 375                 380

Arg Gly Ala Phe Tyr Gly Gly Gly Gly Val Gln Phe Phe Lys Gln
385                 390                 395                 400
```

```
Leu Val Ala Ala Met Phe Val Ile Gly Trp Asn Leu Val Ser Thr Thr
            405                 410                 415
Ile Ile Leu Leu Val Ile Lys Leu Phe Ile Pro Leu Arg Met Pro Asp
            420                 425                 430
Glu Gln Leu Glu Ile Gly Asp Asp Ala Val His Gly Glu Glu Ala Tyr
            435                 440                 445
Ala Leu Trp Gly Gly Glu Lys Tyr Asp Pro Thr Arg His Gly Ser
        450                 455                 460
Leu Gln Ser Gly Asn Thr Thr Val Ser Pro Tyr Val Asn Gly Ala Arg
465                 470                 475                 480
Gly Val Thr Ile Asn Leu
            485

<210> SEQ ID NO 13
<211> LENGTH: 1656
<212> TYPE: DNA
<213> ORGANISM: Triticum aestivum

<400> SEQUENCE: 13
ctcgtgccga attcggcacg aggctacgtg gccgccggac ggcgaggaca agcaactgag      60
caaggtatag gtaggtagat cagtcgggca agatgtcggt gccggtggcg taccagggga     120
acacgtcggc ggcggtggcc gactggctga acaagggcga acgcgtgg cagctgacgg       180
cgtccacgct ggtgggcctc atgagcgtgc cgggcatggt ggtgctgtac ggcggcgtgg     240
tgaagaagaa gtgggcggtc aactccgcct tcatggcgct ctacgccttc gccgccgtct     300
ggatctgctg gtcgtctgg gcctacaaca tgtccttcgg cgaggagctg ctcccgttct      360
ggggcaaggc cggcccggcg ctcgaccagg ccttcctcgt cggccgcgcc tcgctcccgg     420
ccaccgcgca ctaccgcgca gacggcacgc tcgagacggc catggtggag ccctacttcc     480
ccatggccac cgtcgtctac ttccagtgcg tgttcgccgc catcacgctc atcctggtgg     540
ccgggtcgct gctgggccgc atgagcttcc tggcgtggat gctcttcgtg ccgctctggc     600
tcaccttctc ctacaccgtc ggcgccttct ccgtgtgggg cggcggcttc ctcttccact     660
ggggcgtcat cgactactgc ggcggctacg tcatccacat ccccgccggc gtcgccggct     720
tcaccgccgc gtactgggtc gggccaagga ccaagaagga cagggagagc ttcccgccca     780
acaacatcct gttcgcgctc accggcgccg gctgctgtg gatggggtgg gccgggttca     840
acggcggcgg gccgtacgcg gccaatgtcg actcgtccat ggccatcctg aacaccaaca     900
tctgcacggc ggcgagcctc atcgtctgga cctgcctcga tgccgtcttc ttcaagaagc     960
cctccgtggt cggcgccgtc caggccgtga tcaccggtct cgtctgcatc acgccaggcg    1020
caggtgtcgt gcagggttgg gcggcgctgg ttatgggcgt gctggccggc agtgtgccgt    1080
ggtacaccat gatggtgctc cacaagcgct ccaagctcct tcaacgcgtc gacgacaccc    1140
ttggcgtcat ccacacccac ggcgtcgccg gcctgctggg cggcgtcctc acgggcctct    1200
tcgccgagcc gaacctctgc aatctattcc ttccggtcac caactcccgg ggcgccttct    1260
acggtggtaa cggtgggggcg cagctcggga agcagatcgc cggagcgctc ttcgtgatcg    1320
ggtggaacgt ggtcgtcacg tccattatct gcgtcgtcat ccgccttgtc gtcccgctgc    1380
gcatgtccga ggagaagctc gccattggcg acgacgccgt gcacggcgag gaggcctacg    1440
cgttgtgggg cgatggcgag cactacgatg acaccaagca cggcgccgcc gtcgtgccgg    1500
tgtgattttc tctgctttgc ttccttgtta tgtttgtccc gtctatattg tgtcctgctt    1560
```

```
tattttctct tgtctcttgc cttccaaatg taaatttgta gctcatgtat aatgtgacca    1620
aaattttcat agataaaaaa aaaaaaaaaa aaaaa                                1656

<210> SEQ ID NO 14
<211> LENGTH: 470
<212> TYPE: PRT
<213> ORGANISM: Triticum aestivum

<400> SEQUENCE: 14
```

Met Ser Val Pro Val Ala Tyr Gln Gly Asn Thr Ser Ala Ala Val Ala
1               5                   10                  15

Asp Trp Leu Asn Lys Gly Asp Asn Ala Trp Gln Leu Thr Ala Ser Thr
            20                  25                  30

Leu Val Gly Leu Met Ser Val Pro Gly Met Val Val Leu Tyr Gly Gly
        35                  40                  45

Val Val Lys Lys Lys Trp Ala Val Asn Ser Ala Phe Met Ala Leu Tyr
    50                  55                  60

Ala Phe Ala Ala Val Trp Ile Cys Trp Val Val Trp Ala Tyr Asn Met
65                  70                  75                  80

Ser Phe Gly Glu Glu Leu Leu Pro Phe Trp Gly Lys Ala Gly Pro Ala
                85                  90                  95

Leu Asp Gln Ala Phe Leu Val Gly Arg Ala Ser Leu Pro Ala Thr Ala
            100                 105                 110

His Tyr Arg Ala Asp Gly Thr Leu Glu Thr Ala Met Val Glu Pro Tyr
        115                 120                 125

Phe Pro Met Ala Thr Val Val Tyr Phe Gln Cys Val Phe Ala Ala Ile
    130                 135                 140

Thr Leu Ile Leu Val Ala Gly Ser Leu Leu Gly Arg Met Ser Phe Leu
145                 150                 155                 160

Ala Trp Met Leu Phe Val Pro Leu Trp Leu Thr Phe Ser Tyr Thr Val
                165                 170                 175

Gly Ala Phe Ser Val Trp Gly Gly Gly Phe Leu Phe His Trp Gly Val
            180                 185                 190

Ile Asp Tyr Cys Gly Gly Tyr Val Ile His Ile Pro Ala Gly Val Ala
        195                 200                 205

Gly Phe Thr Ala Ala Tyr Trp Val Gly Pro Arg Thr Lys Lys Asp Arg
    210                 215                 220

Glu Ser Phe Pro Pro Asn Asn Ile Leu Phe Ala Leu Thr Gly Ala Gly
225                 230                 235                 240

Leu Leu Trp Met Gly Trp Ala Gly Phe Asn Gly Gly Pro Tyr Ala
                245                 250                 255

Ala Asn Val Asp Ser Ser Met Ala Ile Leu Asn Thr Asn Ile Cys Thr
            260                 265                 270

Ala Ala Ser Leu Ile Val Trp Thr Cys Leu Asp Ala Val Phe Phe Lys
        275                 280                 285

Lys Pro Ser Val Val Gly Ala Val Gln Ala Val Ile Thr Gly Leu Val
    290                 295                 300

Cys Ile Thr Pro Gly Ala Gly Val Val Gln Gly Trp Ala Ala Leu Val
305                 310                 315                 320

Met Gly Val Leu Ala Gly Ser Val Pro Trp Tyr Thr Met Met Val Leu
                325                 330                 335

His Lys Arg Ser Lys Leu Leu Gln Arg Val Asp Asp Thr Leu Gly Val
            340                 345                 350

Ile His Thr His Gly Val Ala Gly Leu Leu Gly Gly Val Leu Thr Gly

```
                355              360              365
Leu Phe Ala Glu Pro Asn Leu Cys Asn Leu Phe Leu Pro Val Thr Asn
    370                 375                 380

Ser Arg Gly Ala Phe Tyr Gly Gly Asn Gly Gly Ala Gln Leu Gly Lys
385                 390                 395                 400

Gln Ile Ala Gly Ala Leu Phe Val Ile Gly Trp Asn Val Val Thr
                405                 410                 415

Ser Ile Ile Cys Val Val Ile Arg Leu Val Val Pro Leu Arg Met Ser
                420                 425                 430

Glu Glu Lys Leu Ala Ile Gly Asp Asp Ala Val His Gly Glu Glu Ala
            435                 440                 445

Tyr Ala Leu Trp Gly Asp Gly Glu His Tyr Asp Asp Thr Lys His Gly
    450                 455                 460

Ala Ala Val Val Pro Val
465                 470

<210> SEQ ID NO 15
<211> LENGTH: 1928
<212> TYPE: DNA
<213> ORGANISM: Zea mays

<400> SEQUENCE: 15
cccaatcccc tccccctcgc gtatccacac ttttcacacg cgacgccgga gagacagagc    60
gcgcgcgcgc cgaaagatg tcgacgtgcg cggcggacct ggcgccgctg ctcggcccgg    120
cggcggcgaa cgccacggac tacctgtgcg ggcagttcgc ggacacggcc tccgcggtgg    180
acgccacgta cctgctcttc tcggcctacc tcgtgttcgc catgcagctc ggcttcgcca    240
tgctgtgcgc cggctccgtc cgcgccaaga acaccatgaa catcatgctc accaacgtgc    300
tcgacgccgc cgcgggggcg ctcttctact acctcttcgg cttcgccttc gccttcggca    360
cgccctccaa cggcttcatc ggcaagcagt tcttcgggct caagcacctg cccaggaccg    420
gcttcgacta cgacttcttc ctctaccagt gggccttcgc catcgccgcc gcgggcatca    480
cgtcgggctc catcgccgag cggacccagt tcgtcgccta cctcatctac tccgcgttcc    540
tgacggggtt cgtctacccc gtggtgtcgc actggttctg gtccgccgac ggctgggccg    600
gcgccagccg cacgtccggc ccgctgctct tcgggtccgg cgtcatcgac ttcgccggct    660
ccggcgtcgt ccacatggtc ggcggcatcg cggggctgtg gggcgcgctc atcgagggcc    720
cccgcatcgg gcgcttcgac cacgccggcc gctccgtggc gctcaagggc cacagcgcgt    780
cgctcgtggt gctcggcacc ttcctgctgt ggttcggctg gtacgggttc aaccccgggt    840
ccttcaccac catcctcaag tcgtacggcc ccgcgggac cgtccacggg cagtggtcgg    900
ccgtgggccg caccgccgtc accaccaccc tcgccggcag cgtcgccgcg ctcaccacgc    960
tgttcgggaa gcggctccag acgggccact ggaacgtggt ggacgtctgc aacggcctcc   1020
tcggcgggtt cgcggccatc acggcggggt gcagcgtggt ggagccgtgg gcggccgtca   1080
tctgcgggtt cgtgtccgcg tgggtgctca tcggcgccaa cgccctcgcg gcgcgcttca   1140
ggttcgacga cccgctggag gcggcgcagc tgcacggcgg gtgtggcgcc tggggcgtcc   1200
tcttcacggg gctcttcgcg aggcgaaagt acgtggagga gatctacggc gccgggaggc   1260
cctacgggct gttcatgggc ggcggcggga agctcctcgc cgcgcagatc atccagatcc   1320
tggtgatcgc cgggtgggtg agctgcacca tgggcccgct cttctacgcg ctcaagaagc   1380
tgggcctgct gcgcatctcg gccgacgacg agatgtccgg catggacctg acccggcacg   1440
```

-continued

```
gcggcttcgc ctacgtctac cacgacgagg accctggcga caaggccggg gttggtgggt    1500
tcatgctcaa gtccgcgcag aaccgtgtcg agccggcggc ggcggtggcg gcggcgacca    1560
gcagccaggt gtaaaaaaaa aatcaggagc aaattgaaac cgagctgaag ttacgtgctt    1620 gccttttca gtatgttgtc gcgtatcacg tttgaggtgg atcgtatctg ccggtcagta    1680
cgcagtgttt gggcaaatac ttggctactt gggagtcgca agaaattgtg taaattatat    1740
agaggaggat ggcgacgaag cacgcatgtg ttacgtagtt ggggtttgtg tgcacatggt    1800
ggtgggcagg ggctaggaga gggtttatct ttaggttatt ttcgtagtgg aatgaatctt    1860
atgatcggat atccaaaaaa aaaaaaaaaa aaaaaaaaaa aaaaaaaaaa aaaaaaaaaa    1920
aaaaaaaa                                                             1928
```

<210> SEQ ID NO 16
<211> LENGTH: 498
<212> TYPE: PRT
<213> ORGANISM: Zea mays

<400> SEQUENCE: 16

```
Met Ser Thr Cys Ala Ala Asp Leu Ala Pro Leu Leu Gly Pro Ala Ala
 1               5                  10                  15

Ala Asn Ala Thr Asp Tyr Leu Cys Gly Gln Phe Ala Asp Thr Ala Ser
             20                  25                  30

Ala Val Asp Ala Thr Tyr Leu Leu Phe Ser Ala Tyr Leu Val Phe Ala
         35                  40                  45

Met Gln Leu Gly Phe Ala Met Leu Cys Ala Gly Ser Val Arg Ala Lys
     50                  55                  60

Asn Thr Met Asn Ile Met Leu Thr Asn Val Leu Asp Ala Ala Ala Gly
 65                  70                  75                  80

Ala Leu Phe Tyr Tyr Leu Phe Gly Phe Ala Phe Ala Phe Gly Thr Pro
                 85                  90                  95

Ser Asn Gly Phe Ile Gly Lys Gln Phe Gly Leu Lys His Leu Pro
            100                 105                 110

Arg Thr Gly Phe Asp Tyr Asp Phe Phe Leu Tyr Gln Trp Ala Phe Ala
        115                 120                 125

Ile Ala Ala Ala Gly Ile Thr Ser Gly Ser Ile Ala Glu Arg Thr Gln
    130                 135                 140

Phe Val Ala Tyr Leu Ile Tyr Ser Ala Phe Leu Thr Gly Phe Val Tyr
145                 150                 155                 160

Pro Val Val Ser His Trp Phe Trp Ser Ala Asp Gly Trp Ala Gly Ala
                165                 170                 175

Ser Arg Thr Ser Gly Pro Leu Leu Phe Gly Ser Gly Val Ile Asp Phe
            180                 185                 190

Ala Gly Ser Gly Val Val His Met Val Gly Gly Ile Ala Gly Leu Trp
        195                 200                 205

Gly Ala Leu Ile Glu Gly Pro Arg Ile Gly Arg Phe Asp His Ala Gly
    210                 215                 220

Arg Ser Val Ala Leu Lys Gly His Ser Ala Ser Leu Val Val Leu Gly
225                 230                 235                 240

Thr Phe Leu Leu Trp Phe Gly Trp Tyr Gly Phe Asn Pro Gly Ser Phe
                245                 250                 255

Thr Thr Ile Leu Lys Ser Tyr Gly Pro Ala Gly Thr Val His Gly Gln
            260                 265                 270

Trp Ser Ala Val Gly Arg Thr Ala Val Thr Thr Leu Ala Gly Ser
        275                 280                 285
```

-continued

```
Val Ala Ala Leu Thr Thr Leu Phe Gly Lys Arg Leu Gln Thr Gly His
    290                 295                 300

Trp Asn Val Val Asp Val Cys Asn Gly Leu Leu Gly Gly Phe Ala Ala
305                 310                 315                 320

Ile Thr Ala Gly Cys Ser Val Val Glu Pro Trp Ala Ala Val Ile Cys
                325                 330                 335

Gly Phe Val Ser Ala Trp Val Leu Ile Gly Ala Asn Ala Leu Ala Ala
                340                 345                 350

Arg Phe Arg Phe Asp Asp Pro Leu Glu Ala Ala Gln Leu His Gly Gly
            355                 360                 365

Cys Gly Ala Trp Gly Val Leu Phe Thr Gly Leu Phe Ala Arg Arg Lys
    370                 375                 380

Tyr Val Glu Glu Ile Tyr Gly Ala Gly Arg Pro Tyr Gly Leu Phe Met
385                 390                 395                 400

Gly Gly Gly Gly Lys Leu Leu Ala Ala Gln Ile Ile Gln Ile Leu Val
                405                 410                 415

Ile Ala Gly Trp Val Ser Cys Thr Met Gly Pro Leu Phe Tyr Ala Leu
            420                 425                 430

Lys Lys Leu Gly Leu Leu Arg Ile Ser Ala Asp Asp Glu Met Ser Gly
        435                 440                 445

Met Asp Leu Thr Arg His Gly Gly Phe Ala Tyr Val Tyr His Asp Glu
    450                 455                 460

Asp Pro Gly Asp Lys Ala Gly Val Gly Gly Phe Met Leu Lys Ser Ala
465                 470                 475                 480

Gln Asn Arg Val Glu Pro Ala Ala Ala Val Ala Ala Ala Thr Ser Ser
                485                 490                 495

Gln Val
```

US 7,692,064 B2

NITROGEN TRANSPORT METABOLISM

This application is a divisional of application Ser. No. 11/514,123 filed Aug. 31, 2006, now U.S. Pat. No. 7,368,634, which is a divisional of application Ser. No. 11/012,668, filed Dec. 15, 2004, now abandoned, which is a continuation-in-part of application Ser. No. 10/033,109, filed Dec. 28, 2001, now U.S. Pat. No. 6,833,492, which is a divisional of U.S. application Ser. No. 09/384,625, filed Aug. 27, 1999, now abandoned, which claims the benefit of U.S. Provisional Application No. 60/098,248, filed Aug. 28, 1998, the entire contents of which are hereby incorporated by reference.

FIELD OF THE INVENTION

This invention is in the field of plant molecular biology. More specifically, this invention pertains to nucleic acid fragments encoding ammonium transporters in plants and seeds.

BACKGROUND OF THE INVENTION

Higher plants are autotrophic organisms that can synthesize all of their molecular components from inorganic nutrients obtained from the local environment. Nitrogen is a key element in many compounds present in plant cells. It is found in the nucleoside phosphates and amino acids that form the building blocks of nucleic acids and proteins, respectively. Availability of nitrogen for crop plants is an important limiting factor in agricultural production, and the importance of nitrogen is demonstrated by the fact that only oxygen, carbon, and hydrogen are more abundant in higher plant cells. Nitrogen present in the form of ammonia or nitrate is readily absorbed and assimilated by higher plants.

Nitrate is the principal source of nitrogen that is available to higher plants under normal field conditions. Thus, the nitrate assimilation pathway is the major point of entry of inorganic nitrogen into organic compounds (Hewitt et al. (1976) Plant Biochemistry, pp 633-6812, Bonner, and Varner, eds. Academic Press, NY). Although nitrate is generally the major form of nitrogen available to plants, some plants directly utilize ammonia, under certain conditions.

In *Saccharomyces cerevisiae*, the transport of ammonium across the plasma membrane for use as a nitrogen source is mediated by at least two functionally distinct transport systems. Expression of an *Arabidopsis* cDNA in a mutant yeast strain deficient in two ammonium uptake systems allowed the identification of a plant ammonium transporter. The isolated cDNA encodes a highly hydrophobic protein with 9-12 putative membrane spanning regions. Sequence homologies to genes of bacterial and animal origin indicated that this type of transporter is conserved over a broad range of organisms suggesting that this gene encodes a high-affinity ammonium transporter (Ninneman et al. (1994) *EMBO J.* 13:3464-3471). A gene encoding an ammonium transporter has been identified in yeast which is most highly expressed when the cells are grown on low concentrations of ammonium or on 'poor' nitrogen sources like urea or proline. This gene is down-regulated when the concentration of ammonium is high or when other 'good' nitrogen sources like glutamine or asparagine are supplied in the culture medium. The main function of this gene appears to be to enable cells grown under nitrogen-limiting conditions to incorporate ammonium present at relatively low concentrations in the growth medium (Marine et al. (1994) *EMBO J.* 13:3456-3463).

Genes encoding high affinity ammonium transporters have yet to be identified in corn, soybean and wheat, although ESTs encoding peptides with similarities to cDNAs encoding high-affinity ammonium transporters are found in the NCBI database. Rice ESTs having General Identifier Nos. 568344 and 2309655 encode peptides with similarities to high-affinity ammonium transporters. Genes encoding ammonium transporters have yet to be identified in corn, rice, soybean and wheat, although an EST encoding a peptide with similarities to cDNAs encoding ammonium transporters is found in the NCBI database having NCBI General Identifier No. 5005512.

SUMMARY OF THE INVENTION

The instant invention relates to isolated polynucleotides, each polynucleotide comprising a nucleotide sequence encoding a first polypeptide that has at least 90% identity based on Clustal method of alignment compared to a polypeptide selected from the group consisting of a corn ammonium transporter polypeptide of SEQ ID NO:2, a soybean ammonium transporter polypeptide of SEQ ID NO:4, a wheat ammonium transporter polypeptide of SEQ ID NO:6, a corn ammonium transporter of SEQ ID NO:8, a rice ammonium transporter SEQ ID NO:10, a soybean ammonium transporter of SEQ ID NO:12, and wheat ammonium transporter of SEQ ID NO:14 and at least 95% identity based on Clustal method of alignment compared to a full length corn ammonium transporter of SEQ ID NO:16. The present invention also comprises an isolated polynucleotide comprising the complement of the nucleotide sequences described above.

The present invention relates to an isolated host cell comprising an isolated polynucleotide comprising a nucleotide sequence of at least 30 contiguous nucleotides derived from a nucleotide sequence selected from the group consisting of SEQ ID NO:1, 3, 5, 7, 9, 11, 13, 15 and the complement of such nucleotide sequences. Suitable host cells include eucaryotic cells such as yeast, and plant cells and procaryotic cells such as bacteria. The present invention also relates to an isolated host cell comprising an isolated polynucleotide comprising a nucleotide sequence encoding a first polypeptide that has at least 90% identity based on Clustal method of alignment compared to a polypeptide selected from the group consisting of a corn ammonium transporter polypeptide of SEQ ID NO:2, a soybean ammonium transporter polypeptide of SEQ ID NO:4, a wheat ammonium transporter polypeptide of SEQ ID NO:6, a corn ammonium transporter of SEQ ID NO:8, a rice ammonium transporter SEQ ID NO:10, a soybean ammonium transporter of SEQ ID NO:12 and wheat ammonium transporter of SEQ ID NO:14 and at least 95% identity based on Clustal method of alignment compared to a full length corn ammonium transporter of SEQ ID NO:16. The present invention also comprises host cells comprising an isolated polynucleotide comprising the complement of the nucleotide sequences described above.

The present invention relates to a recombinant DNA construct comprising an isolated polynucleotide comprising a nucleotide sequence (and its complement) encoding a first polypeptide that has at least 90% identity based on Clustal method of alignment compared to a polypeptide selected from the group consisting of a corn ammonium transporter polypeptide of SEQ ID NO:2, a soybean ammonium transporter polypeptide of SEQ ID NO:4, a wheat ammonium transporter polypeptide of SEQ ID NO:6, a corn ammonium transporter of SEQ ID NO:8, a rice ammonium transporter SEQ ID NO:10, a soybean ammonium transporter of SEQ ID NO:12 and wheat ammonium transporter of SEQ ID NO:14 and at least 95% identity based on Clustal method of alignment compared to a full length corn ammonium transporter of SEQ ID NO:16, operably linked to suitable regulation sequences. The present invention also relates to a recombinant DNA construct comprising a nucleotide sequence of at least 30 contiguous nucleotides derived from a nucleotide sequence selected from the group consisting of SEQ ID NO:1, 3, 5, 7, 9, 11, 13, 15 and the complement of such nucleotide sequences.

The present invention relates to a virus, preferably a baculovirus comprising an isolated polynucleotide comprising a nucleotide sequence encoding a first polypeptide that has at least 90% identity based on Clustal method of alignment compared to a polypeptide selected from the group consisting of a corn ammonium transporter polypeptide of SEQ ID NO:2, a soybean ammonium transporter polypeptide of SEQ ID NO:4, a wheat ammonium transporter polypeptide of SEQ ID NO:6, a corn ammonium transporter of SEQ ID NO:8, a rice ammonium transporter SEQ ID NO:10, a soybean ammonium transporter of SEQ ID NO:12 and wheat ammonium transporter of SEQ ID NO:14 and at least 95% identity based on Clustal method of alignment compared to a full length corn ammonium transporter of SEQ ID NO:16. The present invention also relates to a virus comprises an isolated polynucleotide comprising the complement of the nucleotide sequences described above. The present invention also relates to a virus comprising a nucleotide sequence of at least 30 contiguous nucleotides derived from a nucleotide sequence selected from the group consisting of SEQ ID NO:1, 3, 5, 7, 9, 11, 13, 15 and the complement of such nucleotide sequences.

The present invention relates to an ammonium transporter polypeptide comprising at least 90% homology based on Clustal method of alignment compared to a polypeptide selected from the group consisting of SEQ ID NO:2, 4, 6, 8, 10, 12 and 14 and and at least 95% identity based on Clustal method of alignment compared to a full length corn ammonium transporter of SEQ ID NO:16.

The present invention relates to a process for producing an isolated host cell comprising a recombinant DNA construct of the present invention described above, the process comprising either transforming or transfecting an isolated compatible host cell with a recombinant DNA construct of the present invention.

The present invention relates to a method of selecting an isolated polynucleotide that affects the level of expression of ammonium transporter polypeptide in a plant cell, the method comprising the steps of:

constructing an isolated polynucleotide comprising a nucleotide sequence of at least 30 contiguous nucleotides derived from a nucleotide sequence selected from the group consisting of SEQ ID NO:1, 3, 5, 7, 9, 11, 13, 15 and the complement of such nucleotide sequences;
introducing the isolated polynucleotide into a plant cell;
measuring the level of ammonium transporter polypeptide in the plant cell containing the polypeptide; and
comparing the level of ammonium transporter polypeptide in the plant cell containing the isolated polynucleotide with the level of ammonium transporter polypeptide in a plant cell that does not contain the recombinant DNA construct.

The present invention relate to a method of selecting an insolated polynucleotide that affects the level of expression of ammonium transporter polypeptide in a plant cell comprising the steps described above; however, the isolated polynucleotide comprises a nucleotide sequence encoding a first polypeptide that has at least 90% identity based on Clustal method of alignment compared to a polypeptide selected from the group consisting of a corn ammonium transporter polypeptide of SEQ ID NO:2, a soybean ammonium transporter polypeptide of SEQ ID NO:4, a wheat ammonium transporter polypeptide of SEQ ID NO:6, a corn ammonium transporter of SEQ ID NO:8, a rice ammonium transporter SEQ ID NO:10, a soybean ammonium transporter of SEQ ID NO:12 and wheat ammonium transporter of SEQ ID NO:14 and at least 95% identity based on Clustal method of alignment compared to a full length corn ammonium transporter of SEQ ID NO:16. The above methods may also use isolated polynucleotide comprising the complement of the nucleotide sequences described above.

BRIEF DESCRIPTION OF THE SEQUENCE LISTING

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821-1.825.

TABLE 1

Ammonium Transporters

| Protein | Clone Designation | SEQ ID NO: (Nucleotide) | (Amino Acid) |
|---|---|---|---|
| Corn high affinity ammonium transporter | cr1n.pk0169.g8 | 1 | 2 |
| Soybean high affinity ammonium transporter | sfl1.pk0070.e12 | 3 | 4 |
| Wheat high affinity ammonium transporter | wlm12.pk0020.b10 | 5 | 6 |
| Corn ammonium transporter | p0126.cnlds55r | 7 | 8 |
| Rice ammonium transporter | rl0n.pk083.f9 | 9 | 10 |
| Soybean ammonium transporter | src3c.pk003.h14 | 11 | 12 |
| Wheat ammonium transporter | wlk8.pk0013.b6 | 13 | 14 |
| Corn ammonium transporter | cnr1c.pk002.e24f:fis | 15 | 16 |

The Sequence Listing contains the one letter code for nucleotide sequence characters and the three letter codes for amino acids as defined in conformity with the IUPAC- IUBMB standards described in *Nucleic Acids Research* 13:3021-3030 (1985) and in the *Biochemical Journal* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA, may comprise one or more segments of cDNA, genomic DNA or synthetic DNA.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, polynucleotide comprising a nucleotide sequence of at least 30 contiguous nucleotides derived from a nucleotide sequence selected from the group consisting of SEQ ID NO:1, 3, 5, 7, 9, 11, 13 and the complement of such nucleotide sequences may be used in methods of selecting an isolated polynucleotide that affects the expression of the ammonium transporter polypeptide in a plant cell.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403-410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Recombinant DNA construct" refers any gene that is not a native gene, comprising regulatory and coding sequences that are not found together in nature. Accordingly, a recombinant DNA construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or recombinant DNA constructs. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature (London)* 327:70-73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several ammonium transporters have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other high affinity ammonium transporters or ammonium transporters, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least 30 contiguous nucleotides derived from a nucleotide sequence selected from the group consisting of SEQ ID NO:1, 3, 5, 7, 9, 11, 13 and the complement of such nucleotide sequences may be used in methods of obtaining a nucleic acid fragment encoding a substantial portion of an amino acid sequence encoding an ammonium transporter.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of nitrogen transport and accumulation in those cells. Nitrogen deficiency in plants results in stunted growth, and many times in slender and often woody stems. In many plants the first signal of nitrogen deficiency is chlorosis (yellowing of the leaves).

Overexpression of the proteins of the instant invention may be accomplished by first making a recombinant DNA construct in which the coding region is operably linked to a promoter capable of directing expression of a gene in the desired tissues at the desired stage of development. For reasons of convenience, the recombinant DNA construct may comprise promoter sequences and translation leader sequences derived from the same genes. 3' Non-coding sequences encoding transcription termination signals may also be provided. The instant recombinant DNA construct may also comprise one or more introns in order to facilitate gene expression.

Plasmid vectors comprising the instant recombinant DNA construct can then be made. The choice of plasmid vector is dependent upon the method that will be used to transform host plants. The skilled artisan is well aware of the genetic elements that must be present on the plasmid vector in order to successfully transform, select and propagate host cells containing the recombinant DNA construct. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the recombinant DNA construct described above may be further supplemented by altering the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.* 100:1627-1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a recombinant DNA construct designed for co-suppression of the instant polypeptide can be constructed by linking a gene or gene fragment encoding that polypeptide to plant promoter sequences. Alternatively, a recombinant DNA construct designed to express antisense RNA for all or part of the instant nucleic acid fragment can be constructed by linking the gene or gene fragment in reverse orientation to plant promoter sequences. Either the co-suppression or antisense recombinant DNA constructs could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different recombinant DNA constructs utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a recombinant DNA construct for production of the instant polypeptides. This recombinant DNA construct could then be introduced into appropriate microorganisms via transformation to provide high level expression of the encoded ammonium transporter. An example of a vector for high level expression of the instant polypeptides in a bacterial host is provided (Example 7).

Additionally, the instant polypeptides can be used as targets to facilitate design and/or identification of inhibitors of those enzymes that may be useful as herbicides. This is desirable because the polypeptides described herein catalyze various steps in nitrogen uptake. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bematzky and Tanksley (1986) *Plant Mol. Biol. Reporter* 4(1):37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319-346, and references cited therein).

In another embodiment, nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred KB; see Laan et al. (1995) *Genome Research* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nature Genetics* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402-9406; Koes et al. (1995) *Proc. Natl. Acad. Sci USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
|␣cr1n | Corn Root From 7 Day Old Seedlings* | cr1n.pk0169.g8 |
| cnr1c | Plants were Nitrogen starved until all seed reserves were depleted of a Nitrogen source. Plants were induced with addition of Nitrogen, then samples were collected at 30 min-1 hr and 2 hr after Nitrogen. | cnr1c.pk002.e24.f:fis |
| p0126 | Corn Leaf Tissue From V8-V10 Stages**, Night-Harvested, Pooled | p0126.cnlds55r |
| rl0n | Rice 15 Day Old Leaf* | rl0n.pk083.f9 |
| sfl1 | Soybean Immature Flower | sfl1.pk0070.e12 |
| src3c | Soybean 8 Day Old Root Infected With Cyst Nematode | src3c.pk003.h14 |
| wlk8 | Wheat Seedlings 8 Hours After Treatment With Herbicide*** | wlk8.pk0013.b6 |
| Wlm12 | Wheat Seedlings 12 Hours After Inoculation With *Erysiphe graminis f.* sp *tritici* | wlm12.pk0020.b10 |

*These libraries were normalized essentially as described in U.S. Pat. No. 5,482,845, incorporated herein by reference.
**Corn developmental stages are explained in the publication "How a corn plant develops" from the Iowa State University Coop. Ext. Service Special Report No. 48 reprinted June 1993.
***Application of 6-iodo-2-propoxy-3-propyl-4(3H)-quinazolinone; synthesis and methods of using this compound are described in U.S. Ser. No. 08/545,827, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Example 2

Identification of cDNA Clones cDNA clones encoding ammonium transporters were identified by conducting BLAST (Basic Local Alignment Search Tool; Altschul et al. (1993) *J. Mol. Biol.* 215:403-410;) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266-272) provided by the NCBI. For convenience, the P-value (probability) of observing a match of a cDNA sequence to a sequence contained in the searched databases merely by chance as calculated by BLAST are reported herein as "p Log" values, which represent the negative of the logarithm of the reported P-value. Accordingly, the greater the p Log value, the greater the likelihood that the cDNA sequence and the BLAST "hit" represent homologous proteins.

Example 3

Characterization of cDNA Clones Encoding High Affinity Ammonium Transporter

The BLASTX search using the EST sequences from clones listed in Table 3 revealed similarity of the polypeptides encoded by the cDNAs to high affinity ammonium transporter from *Oryza sativa* and *Arabidopsis thaliana* (NCBI General Identifier Nos. 2160782 and 1703292, respectively). Shown in Table 3 are the BLAST results for the sequences of the entire cDNA inserts comprising the indicated cDNA clones ("FIS"):

TABLE 3

BLAST Results for Sequences Encoding Polypeptides Homologous to High Affinity Ammonium Transporter

| Clone | Status | NCBI General Identifier No. | BLAST pLog Score |
|---|---|---|---|
| cr1n.pk0169.g8 | FIS | 2160782 | 72.50 |
| cnr1c.pk002.e24.f:fis | CGS | 32488298 | 215.40 |
| sfl1.pk0070.e12 | FIS | 1703292 | 254.00 |
| wlm12.pk0020.b10 | FIS | 2160782 | 254.00 |

Nucleotides 6 through 272 from clone wlm12.pk0020.b10 are 91% identical to nucleotides 64 through 330 of a 334 nucleotide rice EST having NCBI General Identifier No. 568344. Nucleotides 6 through 98 from clone wlm12.pk0020.b10 are 90% identical to nucleotides 71 through 163 of a 305 nucleotide rice EST having NCBI General Identifier No. 2309655. Nucleotides 116 through 236 from clone wlm12.pk0020.b10 are 93% identical to nucleotides 181 through 301 of a 305 nucleotide rice EST having NCBI General Identifier No. 2309655. Nucleotides 1 through 1753 from clone cnr1c.pk002.e24.f:fis are 83% identical to nucleotides 5 through 1768 of a 2044 nucleotide rice sequence having NCBI General Identifier No. 32983741.

The data in Table 4 represents a calculation of the percent identity of the amino acid sequences set forth in SEQ ID NOs:2, 4, 6 and 16 and the *Oryza sativa* sequences (NCBI General Identifier Nos. 2160782 and 32488298 and the *Arabidopsis thaliana* sequence (NCBI General Identifier No 1703292)

TABLE 4

Percent Identity of Amino Acid Sequences Deduced From the Nucleotide Sequences of cDNA Clones Encoding Polypeptides Homologous to High Affinity Ammonium Transporter

| SEQ ID NO. | Percent Identity to | | |
|---|---|---|---|
| | 2160782 | 1703292 | 32488298 |
| 2 | 70.5 | 59.6 | 84.8 |
| 4 | 66.2 | 77.8 | 72.5 |
| 6 | 83.6 | 72.7 | 91.3 |
| 16 | 84.0 | 72.5 | 91.8 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a portion of a corn, an entire soybean and an entire wheat high affinity ammonium transporter. These sequences represent the first corn, soybean and wheat sequences encoding high affinity ammonium transporter.

Example 4

Characterization of cDNA Clones Encoding Ammonium Transporter

The BLASTX search using the EST sequences from clones listed in Table 5 revealed similarity of the polypeptides encoded by the cDNAs to ammonium transporter from *Arabidopsis thaliana* (NCBI General Identifier No. 3335376). Shown in Table 5 are the BLAST results for individual ESTs ("EST"), or the sequences of the entire cDNA inserts comprising the indicated cDNA clones ("FIS"):

TABLE 5

BLAST Results for Sequences Encoding Polypeptides Homologous to Ammonium Transporter

| Clone | Status | BLAST 3335376 pLog Score |
|---|---|---|
| p0126.cnlds55r | EST | 28.30 |
| rl0n.pk083.f9 | FIS | 254.00 |
| src3c.pk003.h14 | FIS | 254.00 |
| wlk8.pk0013.b6 | FIS | 254.00 |

The data in Table 6 represents a calculation of the percent identity of the amino acid sequences set forth in SEQ ID NOs:8, 10, 12 and 14 and the *Arabidopsis thaliana* sequence (NCBI General Identifier No. 3335376).

TABLE 6

Percent Identity of Amino Acid Sequences Deduced From the Nucleotide Sequences of cDNA Clones Encoding Polypeptides Homologous to Ammonium Transporter

| SEQ ID NO. | Percent Identity to 3335376 |
|---|---|
| 8 | 76.2 |
| 10 | 68.2 |
| 12 | 75.6 |
| 14 | 64.0 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a portion of a corn, an entire rice, an entire soybean, and an entire wheat ammonium transporter. These sequences represent the first corn, rice, soybean and wheat sequences encoding ammonium transporters.

Example 5

Expression of Recombinant DNA Constructs in Monocot Cells

A recombinant DNA construct comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a recombinant DNA construct encoding, in the 5' to 3' direction, the maize 27 kD zein promoter, a cDNA fragment encoding the instant polypeptides, and the 10 kD zein 3' region.

The recombinant DNA construct described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 6

Expression of Recombinant DNA Constructs in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a recombinant DNA construct composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Recombinant DNA Construct in Microbial Cells

The cDNAs encoding the instant polypeptides can be inserted into the T7 E. coli expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 8

Evaluating Compounds for Their Ability to Inhibit the Activity of Ammonium Transporters The polypeptides described herein may be produced using any number of methods known to those skilled in the art. Such methods include, but are not limited to, expression in bacteria as described in Example 7, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired.

Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity.

Transformation of *Saccharomyces cerevisiae* ammonium transport mutant 26972c, which lacks high affinity ammonium transporters, with the instant cDNAs encoding ammonium transporters will evaluation of compounds for their ability to inhibit enzymatic activation of the instant polypeptides disclosed herein. Assays may be conducted under well known experimental conditions to test for viability of the transformed yeast stain as presented by Marini et al. (1997). *Mol. Cell. Biol.* 17:4282-4293.

What is claimed is:

1. An isolated polynucleotide comprising:
   (a) a nucleotide sequence encoding a polypeptide having ammonium transporter activity, wherein the amino acid sequence of the polypeptide and the amino acid sequence of SEQ ID NO:14 have at least 90% sequence identity based on the Clustal alignment method, or
   (b) the complement of the nucleotide sequence, wherein the complement and the nucleotide sequence contain the same number of nucleotides and are 100% complementary.

2. The polynucleotide of claim 1 wherein the amino acid sequence of the polypeptide and the amino acid sequence of SEQ ID NO:14 have at least 95% sequence identity based on the Clustal alignment method.

3. The polynucleotide of claim 1 wherein the polypeptide comprises the amino acid sequence of SEQ ID NO:14.

4. The polynucleotide of claim 1 wherein the nucleotide sequence comprises the nucleotide sequence of SEQ ID NO:13.

5. A vector comprising the polynucleotide of claim 1.

6. A recombinant DNA construct comprising the polynucleotide of claim 1 operably linked to a regulatory sequence.

7. A method for transforming a cell comprising transforming a cell with the polynucleotide of claim 1.

8. A cell comprising the recombinant DNA construct of claim 6.

9. A method for producing a plant comprising transforming a plant cell with the polynucleotide of claim 1 and regenerating a plant from the transformed plant cell.

10. A plant comprising the recombinant DNA construct of claim 6.

11. A seed comprising the recombinant DNA construct of claim 6.

* * * * *